United States Patent
Su

(10) Patent No.: US 9,179,840 B2
(45) Date of Patent: Nov. 10, 2015

(54) IMAGING AND LIGHTING OPTICS OF A CONTACT EYE CAMERA

(71) Applicant: Visunex Medical Systems Co. Ltd., Grand Cayman (KY)

(72) Inventor: Wei Su, Sunnyvale, CA (US)

(73) Assignee: Visunex Medical Systems Co. Ltd., Jiangsu (CN)

( * ) Notice: Subject to any disclaimer, the term of this patent is extended or adjusted under 35 U.S.C. 154(b) by 0 days.

(21) Appl. No.: 13/845,069

(22) Filed: Mar. 17, 2013

(65) Prior Publication Data

US 2014/0078467 A1     Mar. 20, 2014

Related U.S. Application Data

(60) Provisional application No. 61/612,306, filed on Mar. 17, 2012.

(51) Int. Cl.
| | | |
|---|---|---|
| A61B 3/15 | (2006.01) | |
| A61B 3/125 | (2006.01) | |
| A61B 3/12 | (2006.01) | |
| A61B 3/13 | (2006.01) | |

(52) U.S. Cl.
CPC ............. *A61B 3/125* (2013.01); *A61B 3/1208* (2013.01); *A61B 3/132* (2013.01); *A61B 3/158* (2013.01)

(58) Field of Classification Search
CPC ...... A61B 3/1208; A61B 3/125; A61B 3/158; A61B 3/132
USPC .......................................... 351/219
See application file for complete search history.

(56) References Cited

U.S. PATENT DOCUMENTS

| | | | |
|---|---|---|---|
| 3,944,341 A | 3/1976 | Pomerantzeff | |
| 4,026,638 A | 5/1977 | Govignon | |
| 4,461,551 A | 7/1984 | Blaha | |
| 5,046,608 A | 9/1991 | Laipply | |
| 5,608,472 A | 3/1997 | Szirth et al. | |
| 5,745,212 A * | 4/1998 | Volk .............................. 351/219 | |
| 5,822,036 A | 10/1998 | Massie et al. | |
| 6,267,752 B1 | 7/2001 | Svetliza | |
| 6,361,167 B1 | 3/2002 | Su et al. | |
| 6,446,795 B1 | 9/2002 | Allen et al. | |
| 6,685,317 B2 | 2/2004 | Su et al. | |

(Continued)

FOREIGN PATENT DOCUMENTS

| | | |
|---|---|---|
| JP | 2002238853 A | 8/2002 |
| WO | WO03/057024 A1 | 7/2003 |

(Continued)

OTHER PUBLICATIONS

American Academy of Ophthalmology; Vision Screening for Infants and Children (Policy Statement); American Association for Pediatric Ophthalmology and Strabismus; 3 pgs; ©2013 (earliest approval date: May 1991).

(Continued)

*Primary Examiner* — Jordan Schwartz
(74) *Attorney, Agent, or Firm* — Shay Glenn LLP

(57) ABSTRACT

The optical design for a contact type portable eye imaging apparatus, including the imaging optics and illumination optics are proposed, which utilizes miniature image sensor and solid state light emitting technology, as the next generation of medical imaging devices, in particular in ophthalmic imaging applications.

10 Claims, 8 Drawing Sheets

(56) References Cited

U.S. PATENT DOCUMENTS

| | | |
|---|---|---|
| 7,048,379 B2 | 5/2006 | Miller et al. |
| 7,357,248 B2 | 4/2008 | Sivakumar et al. |
| 7,445,335 B2 | 11/2008 | Su et al. |
| 7,448,753 B1 | 11/2008 | Chinnock |
| 7,499,634 B2 | 3/2009 | Yogesan et al. |
| 7,621,636 B2 | 11/2009 | Su et al. |
| 7,621,638 B2 | 11/2009 | Su et al. |
| 7,650,064 B2 | 1/2010 | Isogai et al. |
| 7,802,884 B2 | 9/2010 | Feldon et al. |
| 7,815,310 B2 | 10/2010 | Su et al. |
| 7,986,859 B2 | 7/2011 | Fischer |
| 8,002,410 B2 | 8/2011 | Shea |
| 8,118,431 B2 | 2/2012 | Shea et al. |
| 8,328,356 B2 | 12/2012 | Cheng et al. |
| 8,356,900 B2 | 1/2013 | Zhou et al. |
| 8,506,083 B2 | 8/2013 | Zhou et al. |
| 8,518,109 B2 | 8/2013 | Shea et al. |
| 8,777,413 B2 | 7/2014 | Zhou et al. |
| 8,820,929 B2 | 9/2014 | Shea et al. |
| 2002/0097379 A1* | 7/2002 | Goldfain et al. ............. 351/221 |
| 2003/0174211 A1 | 9/2003 | Imaoka et al. |
| 2004/0118431 A1 | 6/2004 | Flynn |
| 2005/0018135 A1 | 1/2005 | Maeda et al. |
| 2005/0270484 A1 | 12/2005 | Maeda et al. |
| 2006/0176447 A1 | 8/2006 | Reis |
| 2008/0071254 A1 | 3/2008 | Lummis et al. |
| 2008/0211420 A1 | 9/2008 | Walker et al. |
| 2009/0153797 A1* | 6/2009 | Allon et al. ................... 351/206 |
| 2009/0211586 A1 | 8/2009 | Shea et al. |
| 2010/0091244 A1 | 4/2010 | Volk |
| 2010/0118270 A1 | 5/2010 | Shea et al. |
| 2010/0228236 A1 | 9/2010 | Muhlhoff et al. |
| 2010/0278394 A1 | 11/2010 | Raguin et al. |
| 2011/0085137 A1* | 4/2011 | Kleen et al. ................... 351/206 |
| 2011/0176109 A1 | 7/2011 | Mann |
| 2011/0299036 A1 | 12/2011 | Goldenholz |
| 2012/0026461 A1 | 2/2012 | Chou et al. |
| 2012/0050683 A1 | 3/2012 | Yates |
| 2012/0092619 A1 | 4/2012 | Rowe |
| 2012/0099077 A1 | 4/2012 | Abt |
| 2012/0224142 A1 | 9/2012 | Cornsweet et al. |
| 2012/0229617 A1 | 9/2012 | Yates et al. |
| 2012/0249748 A1* | 10/2012 | Nagano ........................ 348/47 |
| 2012/0287255 A1 | 11/2012 | Ignatovich et al. |
| 2013/0057828 A1 | 3/2013 | De Smet |
| 2013/0103014 A1 | 4/2013 | Gooding et al. |
| 2013/0235345 A1 | 9/2013 | Ohban |
| 2013/0301003 A1 | 11/2013 | Wells et al. |
| 2014/0055749 A1 | 2/2014 | Zhou et al. |
| 2014/0063455 A1 | 3/2014 | Zhou et al. |
| 2014/0063456 A1 | 3/2014 | Zhou et al. |
| 2014/0063457 A1 | 3/2014 | Zhou et al. |
| 2014/0063459 A1 | 3/2014 | Zhou et al. |
| 2014/0063462 A1 | 3/2014 | Zhou et al. |
| 2014/0063463 A1 | 3/2014 | Zhou et al. |
| 2014/0085603 A1 | 3/2014 | Su et al. |
| 2014/0125949 A1 | 5/2014 | Shea et al. |
| 2015/0009473 A1 | 1/2015 | Su |
| 2015/0021228 A1 | 1/2015 | Su et al. |

FOREIGN PATENT DOCUMENTS

| | | |
|---|---|---|
| WO | WO2006/013579 A1 | 2/2006 |
| WO | WO2010/096756 A1 | 8/2010 |
| WO | WO2011/022803 A1 | 3/2011 |
| WO | WO2012/118907 A2 | 9/2012 |
| WO | WO2012/154278 A1 | 11/2012 |
| WO | WO2013/020092 A1 | 2/2013 |
| WO | WO2013/162471 A1 | 10/2013 |
| WO | WO2013/165689 A1 | 11/2013 |
| WO | WO2014/074573 A1 | 5/2014 |

OTHER PUBLICATIONS

Device Optical; Kowa Genesis-D Hand Held Retinal Camera (product information); 3 pgs.; retrieved Jun. 23, 2014 from the internet (http://www.deviceoptical.com/pd_kowa_genesisd.cfm).

Su et al.; U.S. Appl. No. 14/312,590 entitled "Mechanical Features of an Eye Imaging Apparatus," filed Jun. 23, 2014.

Su; U.S. Appl. No. 14/614,305 entitled "Eye imaging apparatus with a wide field of view and related methods," filed Feb. 4, 2015.

* cited by examiner

IMAGING AND LIGHTING OPTICS OF A CONTACT EYE CAMERA

BACKGROUND OF THE INVENTION

1. Field of the Invention

The present invention is related to an ophthalmic examination apparatus, more particularly a contact eye imaging camera which uses the miniature digital image sensor for imaging and the solid state light emitting devices for lighting.

2. Description of the Prior Art

Several portable contact eye imaging systems have been proposed to photograph the posterior of human eyes (fundus camera) over the years. One of such, as disclosed in U.S. Pat. No. 5,608,472, is confined to use a fiber optical cable to guide the light from a remote light source to a hand held camera, which avoids the heat generated from the high brightness light source. The extension of the fiber cable also forms a circular light illumination device in order to distribute the light uniformly on to the posterior of an eye, as shown in FIG. 1. The details of the fiber optical ring structure are demonstrated in FIG. 2, where the fibers are tightly wrapped around and glued to the imaging optical lens where its exterior surface is tapered off. One of surfaces from the front lens is designed to contact the cornea of the eye with its radius matched to that of the cornea. The end of the concentric fiber ring and the matrix material are grounded and polished to have same radius as that of the contact surface of the front lens. The second embodiment in the FIG. 2, shows a more elaborated design where two concentric fiber rings are implemented with the purpose of increasing the distribution of light to the posterior of the eye, and extending the illuminated area by using different projection angles. However, such design has exhibited its unique difficulty in the manufacturing process and was not materialized in the real products. The improvement for the manufacturability was proposed in the U.S. Pat. No. 5,822,036 later, where a cornea contact glass lens is introduced and bonded to the original front lens, as shown in FIG. 3. The larger size of such contact lens not only provides protection for the fiber optical lighting apparatus, but also allows the use of the light conditioning optics, like Fresnel lens, to control the direction and distribution of the light to the posterior of the eye. The corneal contact lens, which forms a triplet with other two imaging lenses behind it, is then sealed to the shell of the imaging apparatus through its outer edge. Although the improvement in the design is significant, it also comes with its own problems, including for example the limitation on the design of light conditioning optics and the difficulty in achieving reliable sealing for the contact optics. A design for the imaging optics is also proposed in the U.S. Pat. No. 5,822,036, where the light from the posterior of the eye is collected by the contact triplet lens and several imaging lenses behind it to form a secondary image, as shown in FIG. 4. Additional relay optics, which is movable for adjusting the focus of the images, is used to directly form a real image from the secondary image plane onto an imaging sensor, like CCD. Such design is suitable for an imaging apparatus built with rather large imaging sensor, where the size of the imaging optics and the difficulty in making such small optics are not obstacles. However, when a miniature image sensor, together with its special imaging optics, is used in a complex imaging system, a new approach for the optical design must be taken.

In this invention, a new optical imaging apparatus, which is more reliable and portable, is proposed. It will be built with new generation of miniature digital cameras as its core imaging sensors and the high power solid state light emitters as its source.

DETAILED DESCRIPTION

Figure 1:
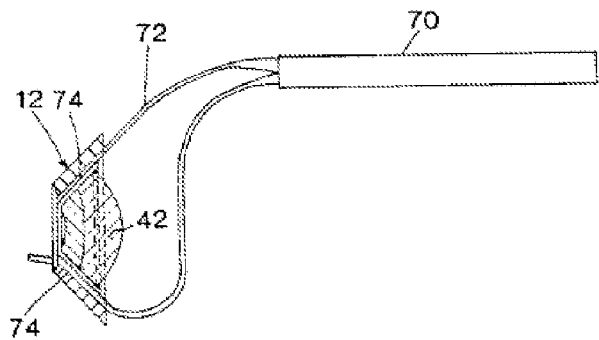
FIG. 1 is the embodiment from prior art where a fiber optical cable is used to guide the light from a remote light source to a hand held camera.
Figure 2:
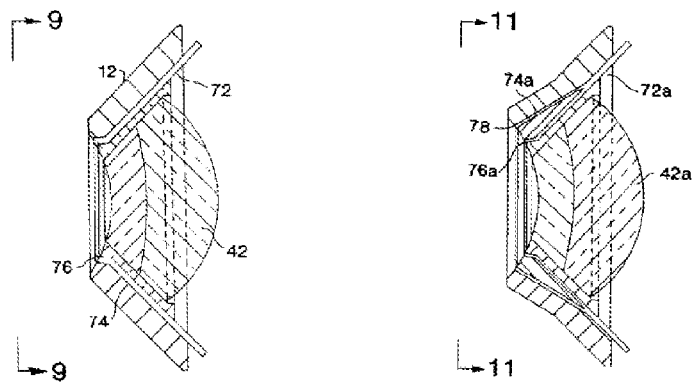
FIG. 2 is the cross sectional view of two embodiments from prior art in which the concentric optical fiber ring is used to illuminate the posterior of an eye.
Figure 3:
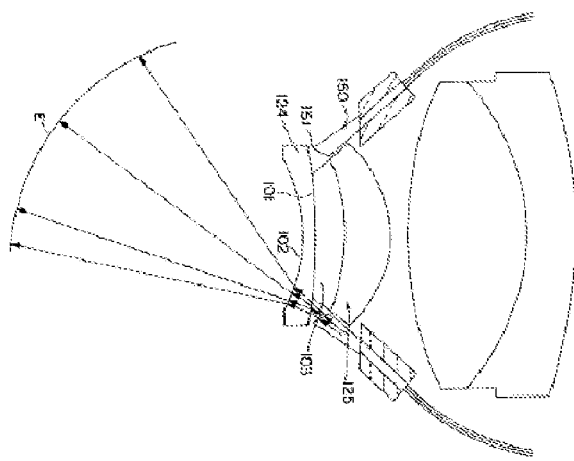
FIG. 3 shows the embodiment from prior art. A corneal contact optical lens is added to the front of the hand held imaging system.
Figure 4:
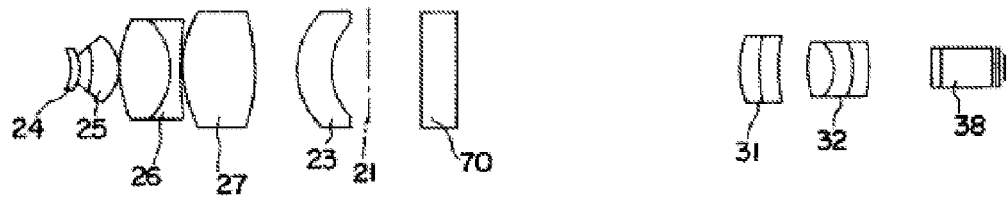
FIG. 4 is the schematic of the optical imaging system from a prior art where a contact lens is added to the imaging optics to form a triplet lens and a large image sensor is used.
Figure 5:
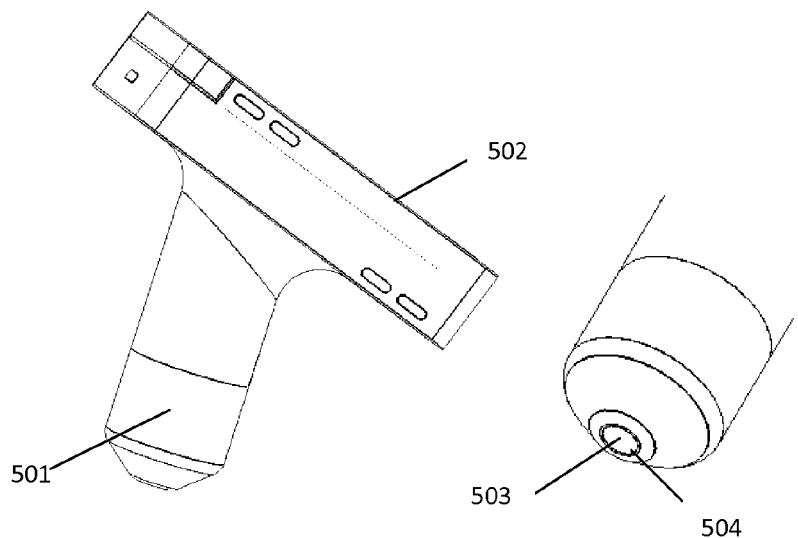
FIG. 5 shows the preferred embodiment for the exterior of a portable contact eye imaging apparatus.

The proposed battery powered and portable imaging apparatus, as shown in FIG. 5, is designed to be carried by the users in a small suite case or in other convenient manners due to its compactness, and to be easily operated by the operators with the minimum training. Its main body is constructed in a cylindrical shape to allow easy grabbing by one hand and with a touch screen display 502 mounted at the top of cylindrical part 501. The users could precisely adjust the position/angle of the apparatus with one hand and free another hand to work on other tasks, for example, opening the eyelids of the patient with the fingers. The captured images could be transferred to other computing devices or internet based devices, like storage unit, through wired or wireless means. The live images could be displayed on the touch screen or watched on larger display which receives data from this imaging apparatus in real time. In its medical applications, it could be used as a diseases screening or medical diagnosis device for the ophthalmic applications, or portable medical imaging device for other medical needs, i.e., ENT or dermatology. The imaging apparatus could be built as one piece or two separated parts, as shown in the FIG. 5. In the later case, the front part of its imaging and lighting optics 501 could be removed or replaced with other functioning modules which contain different optics. When the portion of optics for imaging and lighting is replaced or removed, its potential use or applications could be significantly expanded. A special optical window is exposed from the shell of the imaging apparatus with its center 503 as the entrance for the imaging optics and its peripheral 504 as the window for projecting the illumination light. When it used as an ophthalmic imaging device, for example, the apparatus could be used to take images of posterior portion of the eye with various magnifications and under the illumination from broadband or narrow spectral light sources. To get better quality for the image and wide field of the view (FOV), and the optical window would need to be placed over the cornea of the eye with slight pressure. In this case, the iris of the patient may or may not require to be dilated with the special drugs; and an optically transparent index matching fluid may be placed between the cornea and the optical window. The imaging apparatus also could be used to photograph the anterior of the eye with or without additional optics, with its own lighting or extra external light source(s). The described embodiments of the imaging apparatus could have applications in the areas other than medical, for example, in the security screening applications where the images from the posterior/anterior of the eye could be used for the personal identification purpose.

It is also important to point out that such contact eye imaging apparatus could also be used to image the eyes from other than that of human. For example, it could be used, with or without modification of optics from its human use, to photograph the eyes of horses, cat, dog, rabbit, etc.

Figure 6:
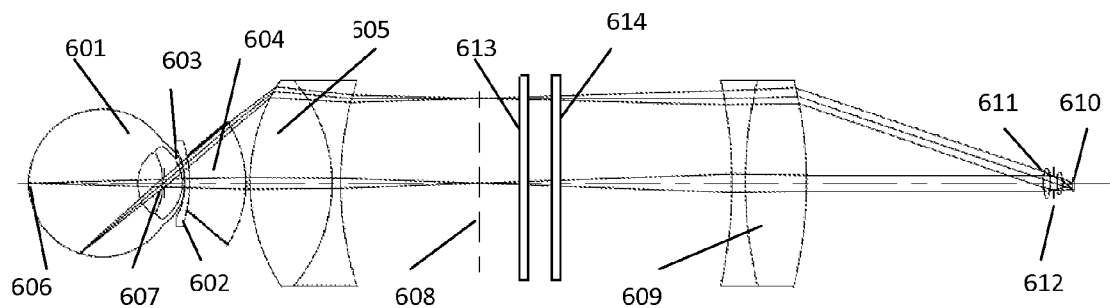
FIG. 6 is the schematic of the optical layout for a preferred wide field of view, posterior eye imaging subsystem where the miniature image sensor and its special imaging optics are integrated as part of the optical system.

The details of the optical schematic are shown in FIG. 6, where the posterior of the eye 601 is photographed by an imaging apparatus with the optical window 602 placed over the cornea 603. An imaging optical lens 604, which could consists of one or multiple lenses, is placed behind the optical window 602. The radius of the curvature for the frontal optical surface of the optical window 602 is chosen to closely match that of the cornea of an eye, and with its back surface flatten out slightly to satisfy the requirement of the optical lighting system which will be discussed in following paragraphs. The window 602 could be made of same or different optical materials as the ones used in lens 604. For a wide angle imaging system, the use of the optical index matching liquid between the optical window 602 and cornea 603 helps to eliminate significant amount of optical aberrations originated from the cornea of the eye. The frontal surface of the optical lens 604 could be same as the back surface of the optical window 602, or slightly different. The back surface of the lens 604 could be made either spherical or none spherical to get the best result for the images. In the embodiment shown in FIG. 6, a small gap of air or other media is placed between the optical window 602 and lens 604, although the two optical components could be in contact in certain areas or even glued together. Together with another optical lens 605, the optical system would gather the light, from the posterior or more specifically the retina of the eye 606, which then passes through the center of the iris opening and the crystalline lens of the eye 607, to form a real image at the secondary image plane 608. The lens 605 could be made of single or multiple lenses, with spherical or none spherical surfaces. In the idea case, the secondary image plane 608 is located near the back focal plane of lens 605. A relay optical lens 609 is used to project the image from the secondary image plane 608 to infinity when the front focal plane of the lens 609 is also placed near the plane 608. A miniature image sensor 610, either in form of CCD, CMOS or other types, with its own image optical lenses 611, is placed near the back focal plane of the optical lens 609 along the optical axis formed by optical lenses before it. The miniature imaging lenses 611 consist of multiple optical lenses and are built with near perfect optical performance. The lenses in the lens group 611 could be moved or adjusted by other means to change its compound optical focal length which results in an optical zoom effect for the images taken or simply the position of the lens group in order to adjust the focus of the images on the image sensor 610. Because the designed objective plane for the imaging lenses 611 is at infinity, the use of such lens could bring the retinal image from the infinity to the image sensor 610 in the optical system shown in FIG. 6. The imaging lens group 611 is built with a circular optical aperture (iris) 612, which could be located between the lenses or just be formed by another aperture plate in the front of the lenses 611. The optical lenses in such imaging system not only could relay the image of the retina 606 to the image sensor 610, but also form the entrance pupil for the imaging system at the surface of crystalline lens 607 when the aperture 612 becomes the aperture of the whole imaging system. The special arrangement helps to eliminate significant amount of scattering light from the anterior chamber of the eye and the optical elements in the imaging system. In the current embodiment, the focusing adjustment of the retinal image on the image sensor 610 could be made by the built-in focusing mechanism from the imaging lenses 611. The auto focus capability for the imaging apparatus could also be realized through same mechanism in the imaging lenses 611 when a close loop control mechanism is implemented. In one embodiment, the focusing status of the retinal image on the image sensor 610 is determined by comparing the sharpness of the image at multiple positions in real time. The size of retinal image could also be changed through the optical zooming function of the imaging lenses 611 in which the effective optical length of the lens group is changeable. In case where the imaging system shown in FIG. 6 is built into two separated parts, it is preferable to install an optical window 613 to seal off the optics from the environment outside, especially to prevent dusts from depositing onto the surface of lens 605 which could be visible in the images. Such window is also necessary if the removable part of the imaging apparatus is built as auto cleavable. Similarly, another optical window 614 could also be installed into the optical path of the imaging system to seal off the rest of optics from dusts and moisture during the sterilizing process. The imaging apparatus therefore could be clearly divided into two pieces between the two optical windows 613 and 614.

It is important to point out that the number of optical components in each lens and their shapes shown FIG. 6 are representative only, and may not be exactly the shape of the preferred embodiment. However, the functions and rough locations of each lens or optical component are well defined. For example, the lens 605 is shown as a cemented doublet and with one concave and one convex out surface in FIG. 6, although it could easily be a group of lenses consisting of one cemented doublet and one air spaced singlet, as long as the design functions the same way as the lens 605 for a doublet.

Figure 7:
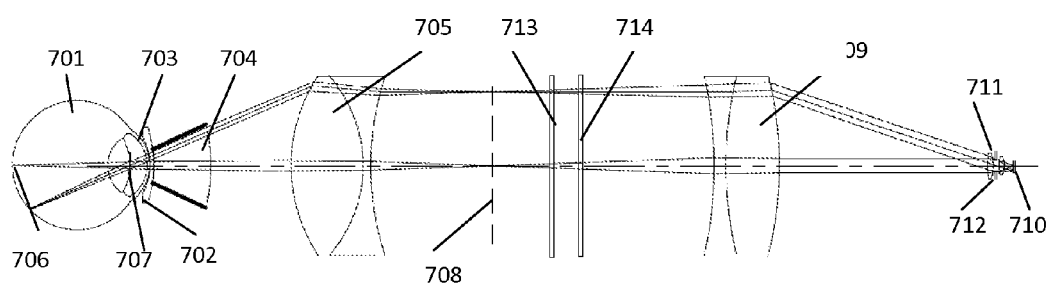
FIG. 7 shows the optical design of a contact posterior imaging subsystem where a posterior eye imaging subsystem with narrower field of view is formed when the front lens set is replaced.

Another embodiment of the invention is shown in FIG. 7, where the front part of the imaging apparatus shown in FIG. 6 is replaced with a new optical subsystem, while the rest of imaging system remains same. In other words, the components shown in FIG. 6 as 609, 610, 611, 612, 613 and 614 are same as the components shown in FIG. 7 as 709, 710, 711, 712, 713, and 714 respectively. The new optical subsystem, represented by optical components 702, 704, 705 and 713, works in similar manner as the one shown in FIG. 6, but generates images with smaller field of view as shown in FIG. 7. The effective focal length of lens 705 is longer than that of lens 605 while the lens 704 also exhibits different shapes. Similar optical subsystems with special features (or designs) could be added as new embodiments to allow the imaging apparatus to work on different eyes or even subjects, for example, adult eye, horse eye, and rabbit eye etc.

Figure 8:
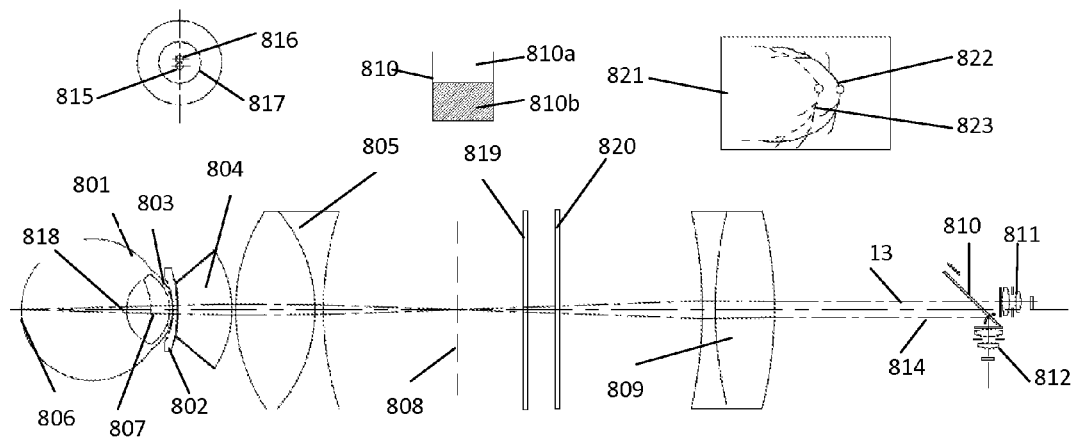
FIG. 8 is the embodiment of optical design for a stereoscopic posterior eye imaging subsystem where two miniature cameras are used to generate 3D images of the retina.

An eye image apparatus, constructed similarly to those embodiments proposed in FIG. 6 and FIG. 7 but is capable of take stereoscopic (3D) images from the posterior of the eye, is demonstrated in FIG. 8. The retina 806 could be photographed when the contact optical window 802 is placed against the cornea 803 of the eye 801. A real image of the retina is formed at the secondary image plane 808 by the optical lenses 804 and 805 after the light from the retina is passed through the center of the crystalline lens 807 in the eye. Two imaging modules 811 and 812, each consists of the imaging optical lenses and the image sensor similar to that in FIG. 6, are placed near the back focal plane of the relay lens 809, while the front focal plane of the lens 809 is near the secondary image plane 808. A beam splitting device 810 is used to divide two separated optical paths for the imaging module 811 and 812 respectively, where equivalently the optical axes 813, 814 of the module 811 and 812 are arranged in parallel but separated by a fixed distance, as shown in FIG. 8. The individual optical apertures in the imaging module 811, 812 are relayed backward by the optical lenses in the imaging system and to form two entrance pupils near the crystalline lens 807. The insert in FIG. 8 shows side view of the dual entrance pupils 815, 816 which are located near the center of the iris opening 817 of the eye. The extension of the optical axes of 813, 814 eventually are converged on to the retina 806 in the eye, and result in a small convergent angle 818. The amount of separation between the optical axes 813, 814 at the imaging modules and subsequently the resulting convergent angle 818 determines the stereosis or stereoscopic effect of the 3D images recorded. Additionally, when images taken from two image sensors, 822, 823, at same time are superimposed on to one screen 821, the focusing status of the retinal images could be measured when the imaging system is correctly calibrated. For example, as seen in the screen frame 821, if the features in the center of two images are not full overlapped, the images are out of focus. Using software to detect the disparity of two images and a close-loop control mechanism, the best focus of the retinal images could be achieved quickly and more precisely by making sure that two images are superimposed to each other. The relative positions of same features in two images, for example, the artery vein in the left image is located at either left or right side of same vein in the right image, could be used to determine the direction of the focus adjustment. The position of each image sensor is pre-calibrated so that the individual image is in focus when two images are fully overlapped. When the captured stereoscopic images are displayed in a 3D screen, users could see the depth of the objects in the posterior of the eye clearly. Similar to the previous embodiments, the optical window 819, 820 could be added to prevent dusts and to build the imaging apparatus autoclave ready. There are several ways to build the beam slitting splitting device 810. In one embodiment, the device 810 is made of total reflective mirror and could be folded down quickly. At the position shown in FIG. 8, the light from eye is guided to the imaging module 812. After one picture is taken by module 812, the device 810 is either folded down or pulled out of its initial position to allow the imaging light to enter the imaging module 811. As the result, two images are recoded sequentially and quickly by two image sensor when all of actions are synchronized. In second embodiment, half of the device 810 is made of transparent and another half reflective, and with the dividing line aligned with the center optical axis of the imaging system. The light from the eye, before reaching the module 811, would pass through the transparent section 810a of device 810, while the light to module 812 would be reflected by reflective half 810b. Here, the shutters of both image sensors could be synchronized to take images simultaneously. In the third embodiment, the two imaging module 811, 812 could be arranged to be side-by-side and with their optical axes in parallel, as long as the separation of the two optical apertures is within the requirement. Although it is preferable to arrange the optical axes of the imaging module 811, 812 in parallel, a small convergent angle could also be used here.

The use of stereoscopic imaging arrangement could also allow implementation of more sophisticated techniques to improve the image quality of retinal images. In one of such embodiments, special software is used to analyze the separation of the suspected artifacts in two stereoscopic images, and then to be compared with the separation of the features on the retina. If the difference in the separation, which is directly related to the distance of the artifacts to the retina in the vitreous, is larger than certain criteria, then the artifacts should be removed from the images. Such artifacts could include unwanted reflection, or haze, from the crystalline lens.

Figure 9:
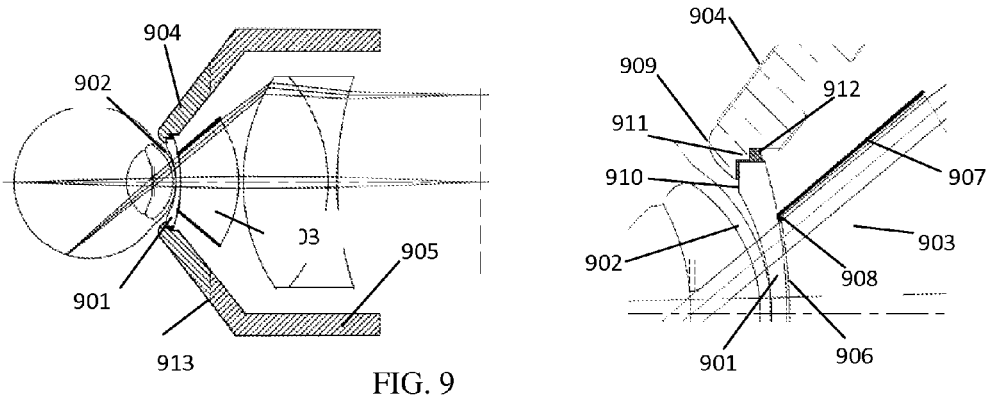
FIG. 9 is the preferred embodiment of a hermetic seal for the front optical window where the window is dropped in from inside during the assembly.

Because the optical window shown in FIG. 6, FIG. 7 and FIG. 8 is in contact with the patients, it is important to provide adequate sealing around its peripheral joint with the shell of the imaging apparatus, in order to prevent cross-contamination by the bacteria. FIG. 9 demonstrates one embodiment of the design where the optical window 901 is in contact with the cornea of eye 902, but separated from the imaging lens 903 with a small gap 906. The surfaces of optical window 901 and lens 903 in both side of the gap 906 would have same or similar radius. The gap 906 could be filled with air or other optically transparent but mechanically elastic materials during the subsequent assembling process. Optical coatings could be applied to the optical surfaces on the both side of the gap 906 to reduce the optical reflectivity if it is necessary. The use of the gap not only allows application of more sophisticated sealing technology, but also adds a compensation space for thermal expansion. The peripheral of the lens 903 is made into a conical shape and coated with optically absorptive material 907 whose absorption spectrum could be in visible range to the eye or extended well into the invisible spectra. The coating 907 could not only prevent the light from entering the lens from outside, but also absorb the straight light from the eye when it enters the lens 903 along with the imaging light. A small absorption ring 908 could be added to the edge of the gap 906 to prevent the light from entering the gap from that particular position. The edge of the gap 906 could also be simply filled with small amount of optical absorption material. The shell 904 of the imaging apparatus, preferably made of metal material, is constructed around the edge of the optical window 901, with smooth edge 909, in order to prevent injury to the patients during the operation. A small flat surface 910, in the form of a circular ring, is added near the edge of the concave surface of the optical window 901. The shell 904 is made to fit with the profile of the optical window 901 at its edge, as shown in FIG. 9, and with small gaps between two components. An alignment edge 911 with even smaller gap is added to help aligning the optical window 901 with the shell 904 more precisely. A larger gap is designed as the reservoir to be filled with hermetic sealing material 912. When the hermetic sealing materials 912 is melted under high temperature, it also fills the smaller gaps between the optical window 901 and shell 904 to provide an air tight seal and strong bonding. To match the thermal expansion properties of optical window material and the shell 904, a special metal material could be used to make section of the shell 904 for the imaging apparatus. In one embodiment, the whole shell could be made of same metal material. In another embodiment, two different metal materials could be used to make the shell. Here, the particular section 904 could then be welded together with the rest of shell 905, which could be made from different material, at the joint 913. To achieve strong joint at 913, in one particular design, part of section 904 is made of same material (or material which could be welded with the material in section 905) as that of section 905 and then bonded together with special treatment, like explosion bonding process. As the result, the contact surface from the section 904 at the joint 913 is made with material which could be is welded with the material in section 905. In another design, a special bonding section is introduced at the joint 913 in the form of a thin wash ring, which is made of two materials. The top surface of the thin ring is made with material which could be welded with section 904, while bottom surface of the thin ring is made with material which is then welded with section 905. The two materials in the thin ring are bonded together with special bonding technique, like explosion bonding process. In another embodiment, the shell section 904 could simply be glued to the section 905.

Figure 10:
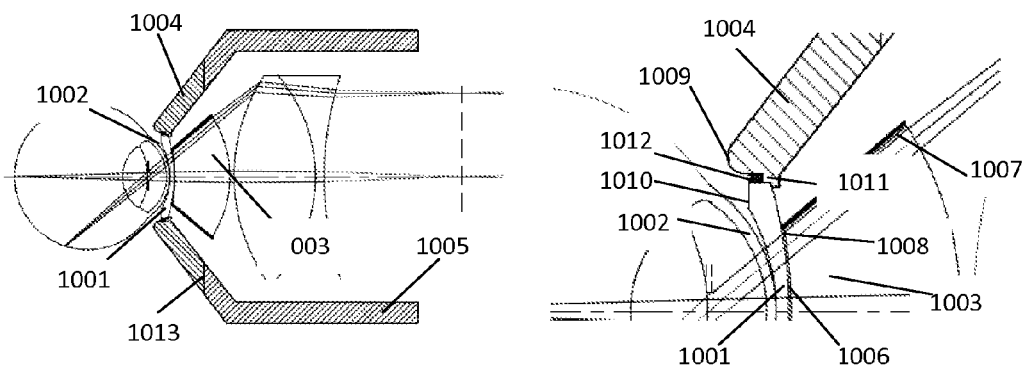
FIG. 10 is the preferred embodiment of a hermetic seal for the front optical window where the window is dropped in from the front during the assembly.

FIG. 10 demonstrates another embodiment of design where hermetic sealing is applied between the optical window 1001 and sell section 1004. The design has similar components as the embodiment shown in FIG. 9. For example, the imaging lens 1003, the absorption coating 1007, the absorption material 1008 and the gap 1006 functions same as 903, 907, 908 and 906 respectively. Special bonding or welding process and design are applied to joint 1013, as well as 913. A small flat surface 1010 is added to the edge of the concave surface of the optical window 1001. The use of the smooth corner 1009 at the end of shell 1004 prevents potential injury to the patients during the operation. The optical window 1001 is designed to be dropped into the cell formed by the shell 1004 from the left side. A small alignment ring 1011 is built into the shell 1004 which is tightly fit with the edge of the optical window 1001, and to provide more precise alignment between the two components. The larger gap between the two components is then filled with hermetic sealing material 1012 under high temperature. Such design not only provides air tight sealing to prevent growth of the bacteria in the small gap or cracks, but also enables strong bonding between the optical window 1001 and shell 1004.

Figure 11:
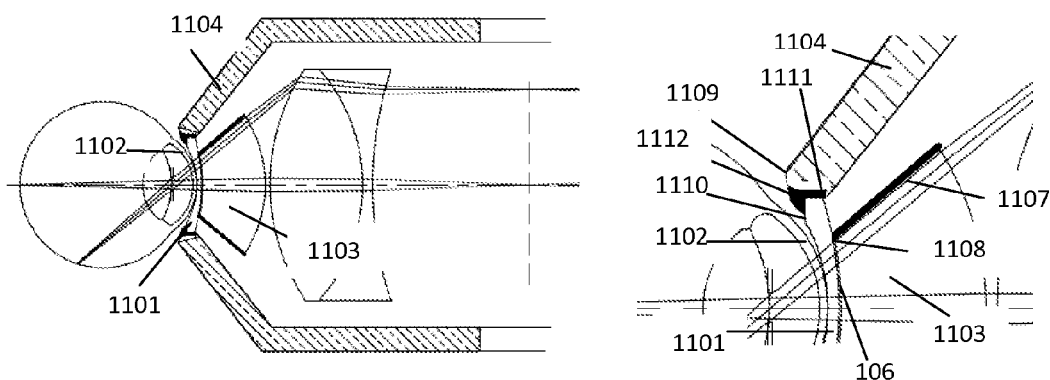
FIG. 11 is the embodiment for the design of front optical window where the adhesive is used to seal the window.

One embodiment of design with more traditional sealing technique is shown in FIG. 11, where the shell 1104 is constructed with one single piece. The designs for the imaging lens 1103, the absorption coating 1107, 1108 and the air gap 1106 are same as components 1003, 1007, 1008 and 1006 demonstrated in FIG. 10. A small flat surface 1110 is added to the edge of the concave surface of the optical window 1101, while an alignment edge 1111 is built in the cell of the shell 1104 to help aligning the optical window 1101. After the optical window 1101 is dropped into the cell, an elastic sealing material 1112 is applied to fill the gap between two components. The round corner 1109 of at the end of the shell 1104 helps to build a smooth transition from the flat surface 1110 to the shell 1104. The sealing material 1112 could be epoxy or UV cured acrylic adhesive.

The embodiments shown in FIG. 9, FIG. 10 and FIG. 11 all employee a special assembly process, where the optical window is aligned and sealed with the shell first. The rest of imaging lenses and lighting fixtures are mounted in a separated unit (module), and then aligned with the frontal optical window. The precision alignment between the optical window and the imaging lenses afterward, as well as setting of the proper gap between the optical window and the imaging lens are critical steps to insure the adequate optical performance of the imaging system. The use of the gap between the optical surfaces helps to reduce the thermal stress and enables the application of more sophisticated hermetic sealing techniques.

Figure 12:
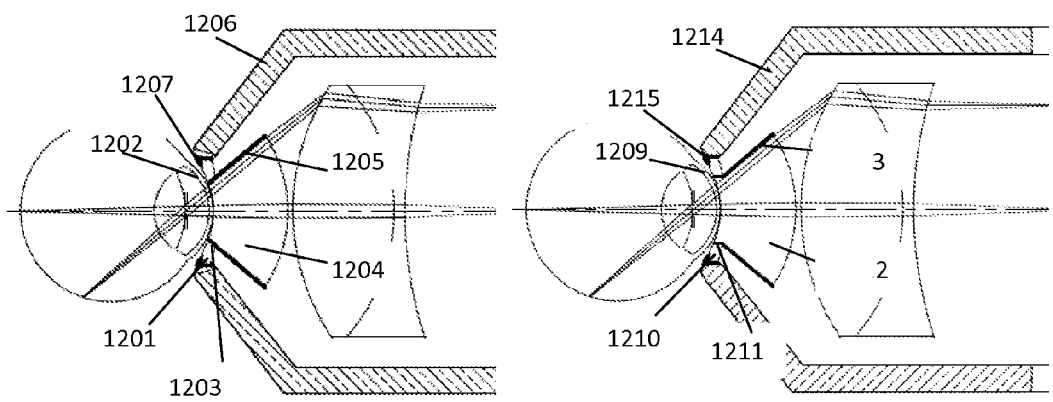
FIG. 12 demonstrates a design for the front optical window where an opening is made in the center of the window.

In another embodiment of the design shown in FIG. 12, an opening 1203 is drilled at the center of the optical window 1201 to allow portion of the imaging lens 1204 to be inserted in. The peripheral of the lens 1204 is made into a conical shape and coated with optically absorptive material 1205 whose absorption spectrum could be in visible range to the eye or extended into the invisible spectra. The coating 1205 not only could prevent light from entering the lens from outside, but also absorb the straight light from the eye when it enters the lens 1204 along with the imaging light. The shape and size of the opening 1203 are made to match that of lens 1204. The concave surface of the optical window 1201 shares same radius as the concave surface of imaging lens 1204. The optical window 1201 is then cemented with the imaging lens 1204, with their concave surface exactly flushed against each other and forms a smooth surface against the cornea of patient 1202. The boundary formed by the absorptive coating provides higher level of separation between lighting optical path and imaging optical path in the imaging lens 1204. An air tight sealing 1207 is applied between the edges of the optical window 1201 and shell 1206, with same technique described in FIG. 11. The front optical window 1201 could be made of optical glass or optically clear polymers.

An embodiment with slightly modified design is also shown in FIG. 12. Here the shape of the tapered opening in the optical window 1210 is straightened out to make it easier for manufacturing. The tip of the imaging lens 1212 is shaped to match that of the opening 1211. Same optical absorptive coating 1213 is applied to the edge of the imaging lens 1212 before the lens 1212 is cemented with the optical window 1210. FIG. 12 shows an air tight sealing 1215 being applied between the edges of the optical window 1210 and shell 1214, with same technique described in FIG. 11. The optical window 1210 could be made of either optical glass or optically clear polymers.

It is important to point out that, although only one example of the air tight sealing is shown in FIG. 11 and FIG. 12, the sealing designs described in FIG. 9 and FIG. 10 could also be applied here.

Figure 13:
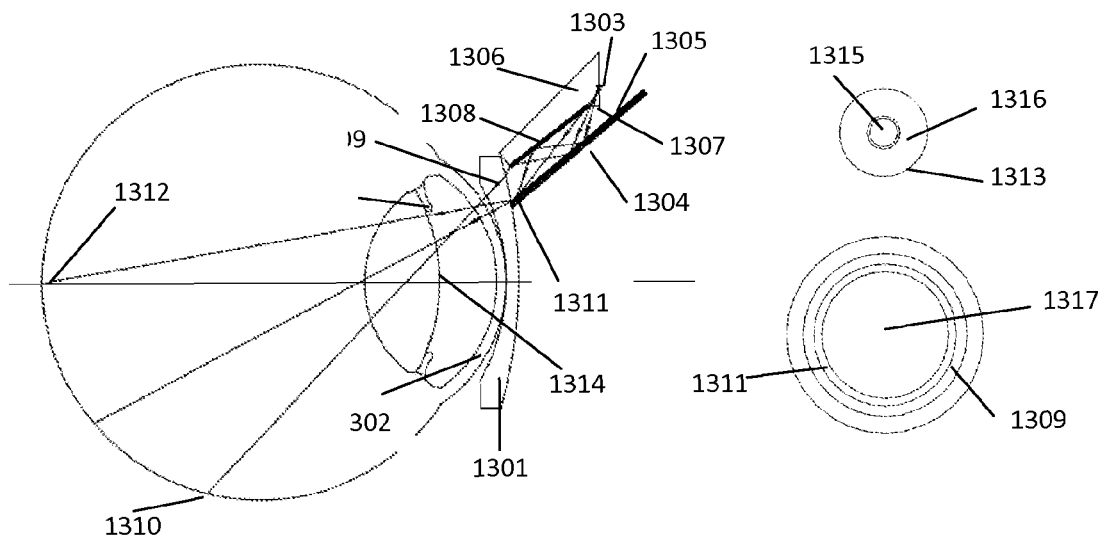
FIG. 13 is the detailed schematic for one embodiment of the light illumination system using a light conditioning device.

To photograph the posterior of the eye, proper lighting must be provided from the imaging apparatus through the proper portion of the natural opening of the eye while avoiding the imaging path. One of such lighting system with optical window similar to that in FIG. 9 is shown in FIG. 13, where the light is projected from behind the optical window 1301 which is in contact with the cornea 1302 of the eye. The light is emitted from a point or ring light source 1303 and then enters an optical light conditioning device 1306 which is defined as an external optical cavity. The device 1306 is made of transparent optical material, and with one of its surface 1308 coated with the optically reflective coating. The device 1306 is suspended with proper space from the edge of the imaging lens 1304. The edge of the imaging lens 1304 is first coated with optically absorptive material described in FIG. 9. An optically reflective coating 1305 is then added on to the top of the absorptive coating. Such special coating produces strong absorption to the straight light within the imaging lens 1304, while reflects illumination light from another side of the coating. The light from the light source 1303 passes through the transparent window 1307 of the device 1306, and enters the external optical cavity formed by two reflective surfaces. After multiple reflections, portion of the light 1309 is projected through the upper edge of the cavity, the optical window 1301 and the cornea 1302, and eventually onto the peripheral area of the retina 1310. Another portion of the light leaves cavity at its lower edge 1311; and then passes through the optical window 1301, the cornea 1302 and finally reaches the central portion of the retina 1312. The location of the lower edge of the cavity 1311 is chosen so that the light emitted from this area is not blocked by the edge of the iris 1313 of the eye. To illustrate the lighting arrangement more clearly, a side view of the optical window 1301 is provided in FIG. 13, where the light from the lower edge of the optical cavity forms a light ring 1311 and the light from the upper edge forms a larger ring 1309. The central portion 1317 of the optical window 1301 is reserved as the optical path for the light returning from the retina as the imaging light. As shown in FIG. 13, it is clear that the lighting path and the imaging path are totally separated at the front optical window 1301. As discussed before, the optical imaging system always form an entrance pupil near the crystalline lens 1314 of the eye. A side view of the anterior surface of the crystalline lens is also shown in the insert of FIG. 13, where entrance pupil 1315 is located at the center of the iris 1313. The illumination light from both upper and lower edge of the optical cavity 1309, 1311 falls on area 1316 which is outside of the entrance pupil 1315. Such optical arrangement creates a separation between the illumination path and the imaging path on the anterior surface of the crystalline lens, and prevents the reflected and scattered light from entering the imaging path and eventually the image sensor. As seen in the insert, a small border area could be created between the illumination zone 1316 and entrance pupil 1315, thus further reducing the cross talk. It is important to point out that the light from the two areas 1309, 1311 of the optical window 1301 would produce an overlapping area for the illumination at the retina, and a relatively uniform lighting condition.

Figure 14:
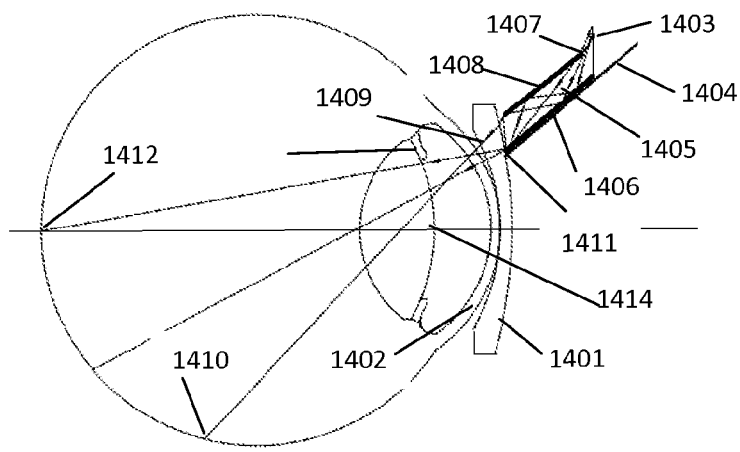
FIG. 14 demonstrates another light conditioning device used in the light illumination system for the posterior imaging.

The light conditioning device 1306 could take many different forms, but still produce same result. One embodiment is shown in FIG. 14, where the conditioning device 1405 is made of solid transparent optical material and formed as an internal optical cavity. Two surfaces, 1406 and 1408, of the device 1405 are coated with optically reflective coating. The edge 1404 of the imaging lens is still coated with optically absorptive material to absorb the straight light from inside of the lens. The light from the light source 1403 enters the device 1405 when it is placed against the light conditioning device 1405. Portion of the light is blocked by the edge 1407 of the reflective coating area 1408, while the majority of the light enters the internal optical cavity formed by two reflective surfaces 1406 and 1408. The portion of the light leaving the cavity at the lower edge 1411 of the cavity will be projected to the central portion 1412 of the retina after passing through the optical window 1401 and the cornea 1402. As discussed in FIG. 13, the portion of the light 1409 from the upper edge of the device 1405 would be used to illuminate the peripheral area of the retina 1410. The optical arrangement for the lighting and the imaging paths on the optical window and crystalline lens of the eye is same as shown in FIG. 13.

Figure 15:
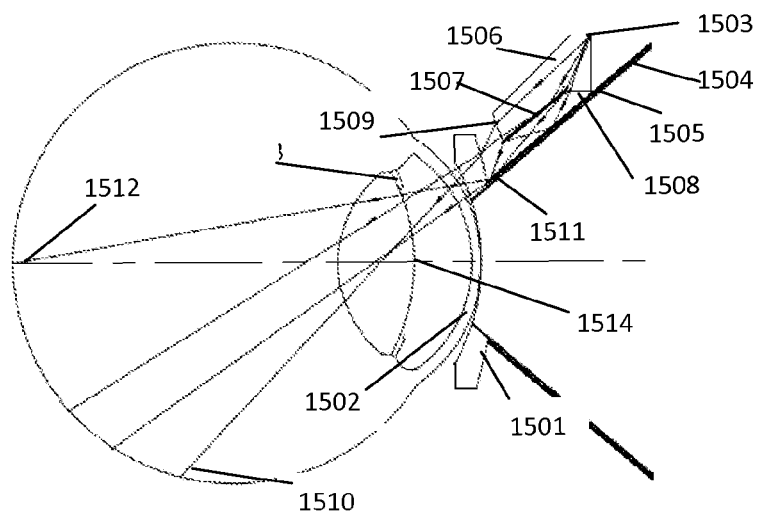
FIG. 15 shows the third design for a light conditioning device.

A third design of light conditioning device, which is constructed by one external and one internal cavity, is shown in FIG. 15. The device 1506 is made of optically transparent material and with one of surface 1507 coated with optically reflective coating so that the surface is reflective from both sides. The edge of the imaging lens is first coated with optically absorptive material 1504 and then coated with an optically reflective coating 1505. The absorptive coating 1504 is used to absorb the straight light inside the imaging lens while the reflective coating 1505 is used by the illumination system. After entering the device 1506, portion of the light from the light source 1503 passes through the transparent window 1508 of the device 1506 and is reflected multiple times by two reflective surface 1505 and 1507. The light leaves the lower edge of the cavity 1511 and is eventually projected on to the central portion 1512 of the retina. Another portion of the light enters the upper chamber (internal optical cavity) of the device 1506 from the light source 1503. As shown in FIG. 15, portion of light could be reflected by the surface 1507 before exit while another portion of the light would directly exit the device 1506 from the transparent window 1509 at the upper edge of the device 1506. The light exited from window 1509 will be guided toward the peripheral area 1510 of the retina. The optical arrangement for the lighting and imaging paths on the optical window 1501 and crystalline lens 1514 of the eye is same as shown in FIG. 13.

Although only one type of design for the frontal optical window is shown in FIG. 13, FIG. 14 and FIG. 15, the light conditioning device and the related lighting design discussed in each embodiment could be applied to other type of frontal optical windows, as discussed in FIG. 9 and FIG. 12.

Figure 16:
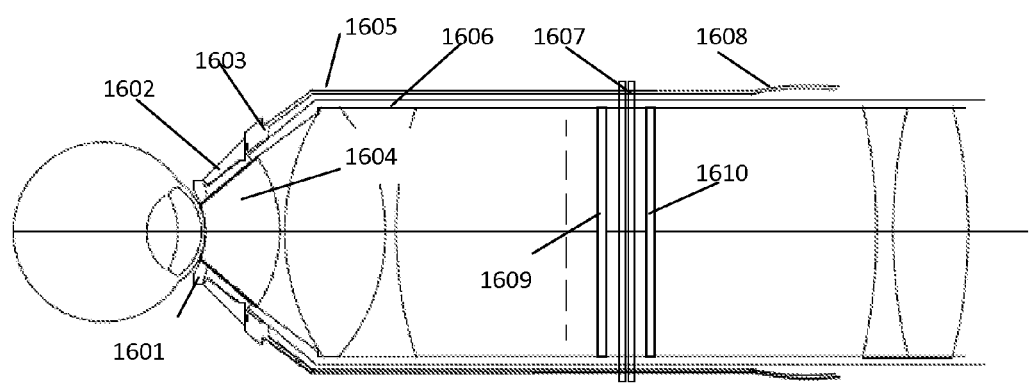
FIG. 16 shows an embodiment for the solid state lighting system in the imaging apparatus where the lighting element is placed directly behind the light conditioning device.

Solid state light emitting devices are used as the light sources in the imaging apparatus discussed in this invention. In the first embodiment of the imaging apparatus, as shown in FIG. 16, the light sources 1603 are placed directly against the light conditioning device 1602. The light source 1603 could include light emitting elements and heat sink which is used to disperse the heat generated by the emitters. The light from light sources is guided into the posterior of the eye through the device 1602 and optical window 1601 in the manners discussed in previous paragraphs. The light sources, together with the heat sink, are placed outside an inner shell 1606 which houses the optical imaging lenses, including the lens 1604. The light sources are powered electrically through the electric wires 1605 laying along the outer surface of the shell

1606. In case where the imaging apparatus is designed with two separated sections, an electric connector 1607 is used to interconnect the wires 1605 and the wires 1608. It is preferable that the more sophisticated electronic drivers for the light sources 1603 are housed in the section in the right side of FIG. 16. The removable section of the imaging apparatus, which contacts with the eye, could be built with various kinds of light emitting elements for the unique lighting requirements and applications. However, those removable imaging modules could be driven by same standard electronic drivers housed in main body of the imaging apparatus, through the electrical interconnector 1607. To prevent dusts entering the shells housing the optics, two optical windows 1609 and 1610 are used to seal off the spaces. If a single body construction is required, then the electric interconnection 1607 and the optical window 1609, 1610 are no longer needed.

Figure 17:
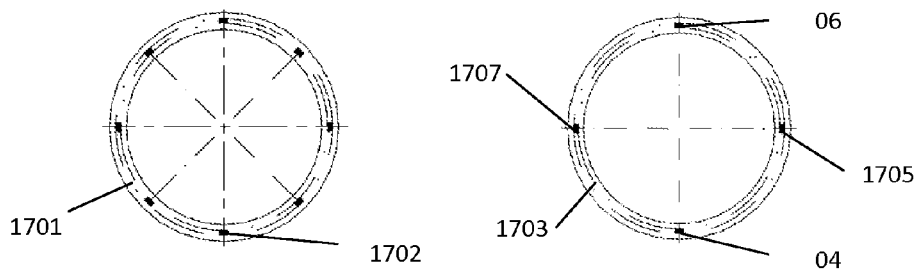
FIG. 17 shows details of the solid state lighting elements and their heat sink.

The location of the light sources shown in FIG. 16 should be distributed evenly in order to provide uniform illumination on the retina. The numbers of the light sources in need could vary, depending on the requirement of the particular application. Two embodiments of the design are demonstrated in FIG. 17, where a total of 8 and 4 light sources are used. In one embodiment, the light emitting elements 1702 is mounted onto a heat sink 1701 which forms a ring to increase its mass and heat dispersion capability. 8 of the elements 1702 are distributed evenly on the heat sink. Those light sources could be lighted up simultaneously and be synchronized with the shutter of the image sensor. It is important to point out that more or less numbers of light elements could be used, even to the point where the light sources actually form a linear line source. In the second embodiment, only 4 light emitting elements 1704, 1705, 1706, 1707 are used and mounted onto the heat sink 1703. Those lighting elements could be lighted up simultaneously or sequentially.

Figure 18:
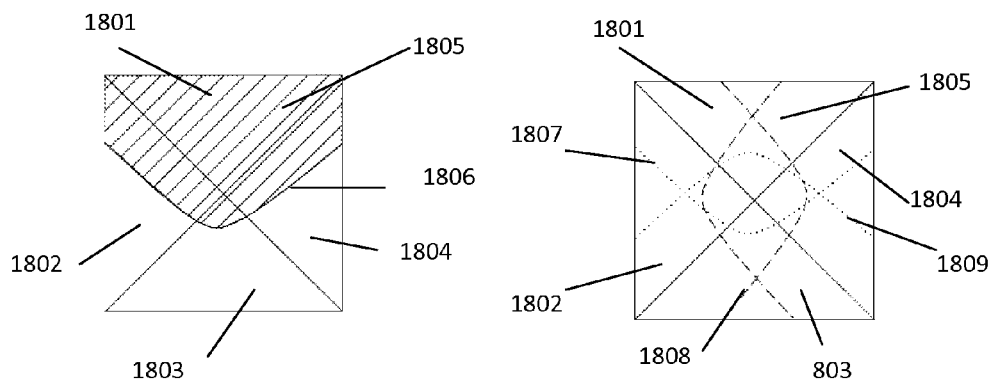
FIG. 18 shows images taken when the lighting elements are lighted up sequentially and the special process is deployed to enhance the image quality.

A unique lighting condition is created when the lighting element is lighted up sequentially. For example, if only lighting element 1704 is lighted up, then a small portion of the retina or posterior of eye is illuminated. As the result, only portion of the image 1801 taken by the image sensor is seen with the adequate illumination, as exemplified in FIG. 18. In the picture 1801, the shaded area which is a bit larger than one quarter 1805 of the image is well lighted, while the majority of quarters 1802, 1803 and 1804 are not lighted up. However, due to the unique scattering characteristic of the eye, the scattered light by the eye would show up mostly in the quarter 1803 in the form of white haze, leaving clear images in the quarter 1805. The brightness of the illuminated area often gradually degreases toward its boundary area 1806, while the brightness of image in the quarter 1805 is relatively uniform. As the next lighting element, for example 1705, is lighted up after 1704, the illuminated area is moved to be centered on the quarter 1802. When all of 4 lighting elements are powered up sequentially, 4 images with uniquely lighted up quarters and sections of clear images are taken. A special image processing scheme is proposed to clear up the white haze from the retinal images with sequential lighting techniques. As shown in picture 1801, when the quarter 1805 is lighted up, only portion of the image within the boundary 1807 is saved. Accordingly, only portion of the image within the boundary 1808 is save when the quarter 1802 is illuminated. Two more images are taken from the quarter 1803, 1804 and their surrounding areas. When all of 4 lighting elements are lighted up sequentially, 4 partial images are obtained as the result. Because the imaging apparatus or the eye could be moved slightly during the imaging session, the features from the 4 partial images may not overlap precisely. The extended area from the border of each quarter is required to allow the proper adjustment and re-alignment of the images by special software algorithm. After the 4 images are aligned precisely, the brightness of the images in the border area is re-adjusted to produce one single image with uniform brightness and color.

The sequential lighting scheme discussed in the previous paragraph could be applied when different numbers of the lighting elements are used. The possible examples include 3 elements, 6 elements or even 8 elements.

Figure 19:
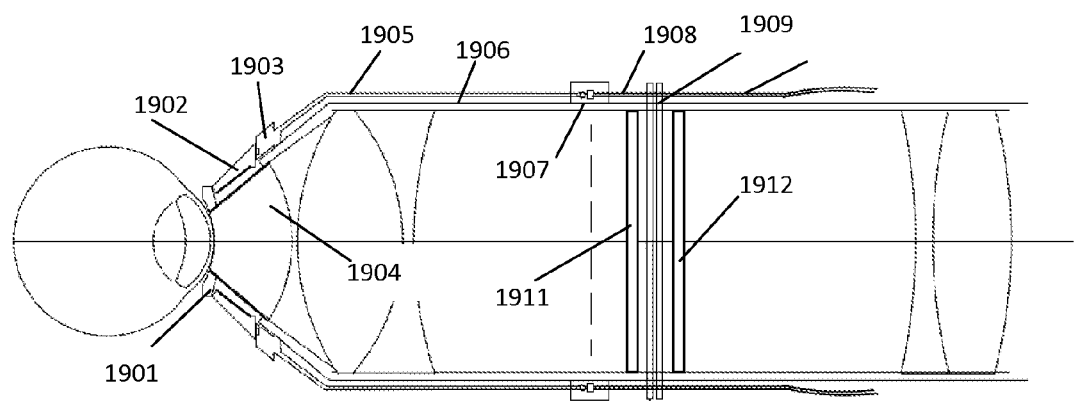
FIG. 19 is a preferred embodiment for the solid state lighting system where the optical fibers are used to transmit light.

In another embodiment of the imaging apparatus, as shown in FIG. 19, the optical fibers 1905 are used to guide the light from the solid state lighting element 1907 to the light conditioning device 1902. The construction for the rest of the imaging apparatus is similar to the one shown in FIG. 16. The power to the lighting elements is provided by the electric wires 1908, which is interconnected with the wires 1910 in the main body of the imaging apparatus through the connector 1909. To prevent dusts entering the shells housing the optics, two optical windows 1911 and 1912 are used to seal off the spaces. If a single body construction is required, then the electric interconnection 1909 and the optical window 1911, 1912 are no longer needed.

Figure 20:
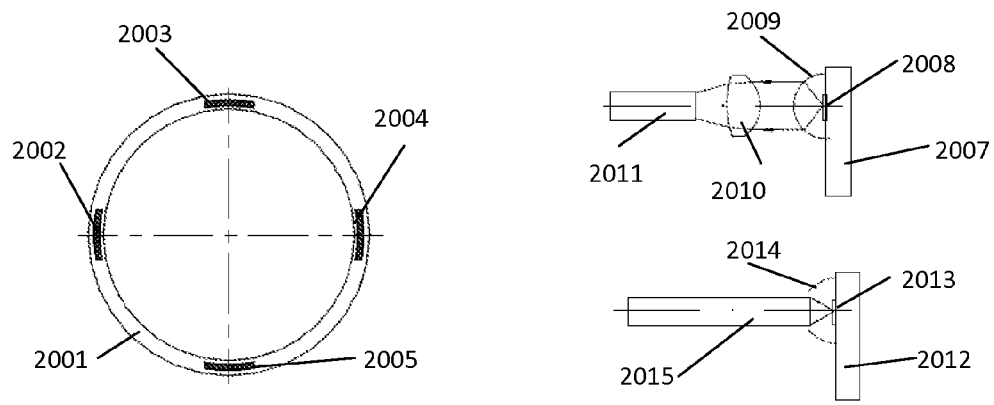
FIG. 20 shows details of the light coupling mechanism and the multiple lighting elements formed by optical fibers indirectly.
Figure 21:
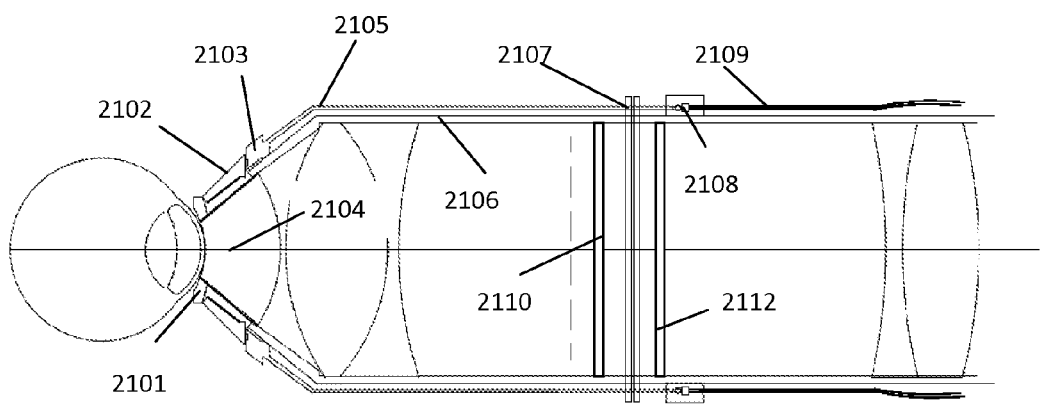
FIG. 21 is the third embodiment for solid state lighting system where the optical fibers are employed and simple optical coupling is used between the optical fibers.

The optical fibers could be used to form multiple lighting elements against the light conditioning device. One example of such design is shown in FIG. 20, where fiber optical elements 2002, 2003, 2004 and 2005 are made into the lighting base 2001 and distributed evenly. The shape and size of each fiber optic lighting element shown in FIG. 20 is mean to demonstrate the concept, not the exact engineering design. Each lighting element, for example 2002, receives light from one solid state lighting element. The number of the fiber optic elements could be other than 4 shown in FIG. 20. Various optical designs would be implemented to increase the optical coupling efficiency, with two examples demonstrated in FIG. 20. In the first design, an optical coupling lens 2010 is used to collect light from the light emitting element 2008 and then relay it into the entrance of an optical fiber bundle 2011. The individual optical fibers in the bundle 2011 is then spread out at the another end of the fiber to form the lighting element. The solid state lighting element often comes with a protective dome 2009 and is mounted onto a ceramic or metal base 2007. The multiple light emitting elements could be mounted to a larger heat sink base through their ceramic/metal bases, in order to increase the heat dispersion capability. The heat sink could also be made to be in contact with the shell of the imaging apparatus in order to disperse the heat. If the heat sink (ring) is built next to the interconnection surface shown in FIG. 19, a matching heat sink made with copper or other materials with good thermal conductivity could be built in the main body section of the imaging apparatus. When the removable section is attached to the main body of the imaging apparatus, the two heat sinks would come to against each other, thus allows easy transfer of the heat from the lighting element to the bigger mass in the main body. Such design would reduce the temperature of the shell where the user holds the imaging apparatus. In the second design, the optical fiber bundle 2015 is directly inserted into the dome 2014 of the solid state lighting element 2013. The direct coupling could produce high efficiency, although the breakdown of seal for the dome could cause problem in certain situation. In the embodiment shown in FIG. 21, the solid state lighting element 2108 is placed in the main body of the imaging apparatus. The light is then guided to the light conditioning device 2102 through optical fiber bundle 2105 and then the new lighting elements 2103. If front section of the imaging apparatus is removable, then an optical coupling mechanism 2107 must be added to couple light from one side to another. The simplest coupling mechanism is to have two fiber bundles aligned to each other and in direct contact. The power of the lighting element 2103 is supplied through the electric wires 2109 by the electronic drivers.

Figure 22:
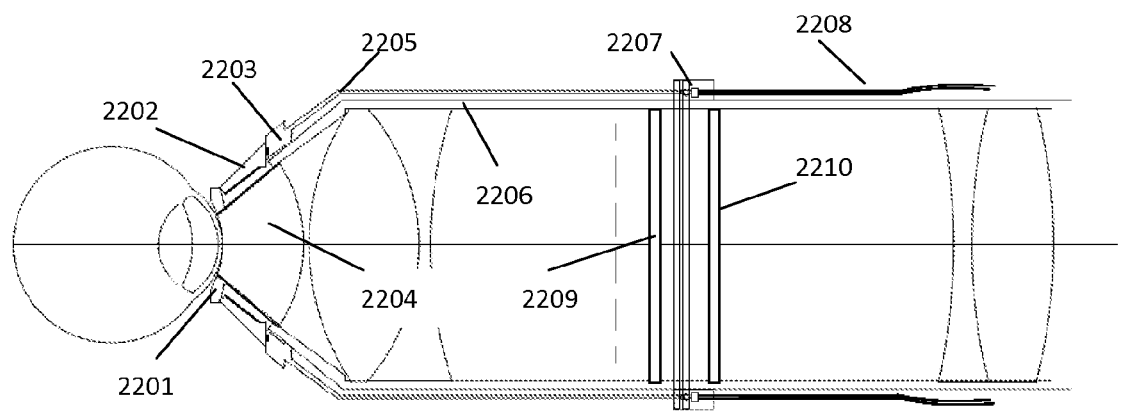
FIG. 22 is the fourth embodiment for solid state lighting system where a more sophisticated optical coupling design is used to increase the light coupling efficiency.
Figure 23:
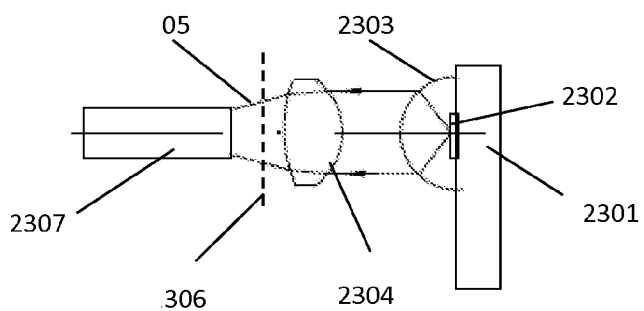
FIG. 23 demonstrates the details of the optical coupling design used between the removable section and main body of the imaging apparatus.

A more sophisticated and efficient coupling design is shown in FIG. 22, where the solid state light emitting element 2207 is located in the main body of the imaging apparatus, but near the interconnection interface. The light is then coupled into the end of the optical fiber bundle 2205 which is located in the removable section of the imaging apparatus, with its end exposed to the outside. The optical fibers, after running from the outside of the lens housing 2206, are used to form the multiple lighting elements 2203. The power of the lighting element 2207 is supplied through the electric wires 2208 by the electronic drivers. The details of the optical coupling mechanism are shown in FIG. 23, where the dash line 2306 represents the interface between the two sections of the imaging apparatus. The light from the solid state light emitting element 2302 is first collimated by its dome lens 2303 and then coupled to fiber bundle 2307 through the coupling lens 2304. The light emitting device with its base 2301 is mounted onto a heat sink base in the main body of the imaging apparatus. The coupling optical lens 2304 is also mounted to the structure in the main body and pre-aligned with the light emitting element 2302. Because the optical fiber bundle 2307 is located in the removable section of the imaging apparatus and does not come into physical contact with optics in the main body, the light beam 2305 is projected into the end of the fiber bundle directly through air. Such arrangement not only increases the optical coupling efficiency of the light, but also avoids the wear out at the end of the optical fiber bundles.

The solid state lighting elements shown in the inventions above could emit the light with broadband spectrum or narrow band spectrum. The light could be visible to human eye with a single color or broadband white color. The light could also be invisible to human eye, for example, in the infrared or near infrared. All of the lighting elements used in one unit could emit same kind of light or even different kinds of light.

In the most common case, the solid state lighting elements emit white color light for the color imaging application. However, in one particular application, the solid state lighting elements could emit light in deep blue color when they are driven by same electrical power supply system from the main body. The blue light would excite the fluorescin dye in the blood vessels of the eye, which in turn emits green light. When the optical window at the end of removable section, which originally is used to protect the optics from dust, is replaced with an optical blocking filter, the green emission light would be collected by the rest of optics in the main body to form an image of fluoresin angiogram. The optical blocking filter reflects/absorbs the blue light, but allows the green emission light to go through. The removable front section of the imaging apparatus with such special features could be built as a special fluoresin angiogram unit. Similarly, another type of angiogram imaging apparatus could be formed when the solid state lighting elements emit near infrared light and the optical blocking filter works in such spectrum too.

The invention claimed is:

1. An eye imaging optical apparatus, comprising:
   a transparent optical window with a frontal surface fit with the profile of the cornea of the eye and coated with a layer of optical reflection reduction coating;
   a transparent optical lens with conical shape located behind the optical window and separated with a small gap, with its conical surface coated with a thin optically absorptive layer, and with its frontal surface made with profile as same or similar to the profile of the back surface of the optical window;
   a first relay optical lens, which comprises one or multiple lenses, to form a real image of the internal eye structures, or fundus near its back focal plane;
   a second relay optical lens, which comprises one or multiple lenses, with its front focal plane located next to the back focal plane of the first relay lens to form the image of the internal structure, or fundus at the infinity;
   a miniature optical lens, which comprises multiple optical lenses, with its optical aperture located near the back focal plane of the second relay lens and along the optical axis formed by the optical lenses before it; and
   a miniature electronic area or image sensor, located at the back focal plane of the miniature optical lens in the front of it, to capture the images of the internal structure of the eye or fundus;
   wherein a real image of the optical aperture of the miniature optical lens is formed near the anterior surface of the crystalline lens of the eye or the iris plane when the eye imaging apparatus is used to photograph the posterior segment of an eye.

2. The eye imaging optical apparatus recited in claim 1 where the gap between the optical window and optical lens behind it is filled with air or optical clear index matching materials.

3. The eye imaging optical apparatus recited in claim 1 wherein the focus of the imaged objects is adjusted by the effectively and internally moving the position of the miniature lens relative to the image sensor.

4. The eye imaging optical apparatus recited in claim 1 wherein the magnification of the images is changed by the effective change of the optical focal length of the miniature lens in the front of the image sensor.

5. The eye imaging optical apparatus recited in claim 1 wherein said eye imaging optical apparatus is used to image the posterior and anterior of an eye.

6. The eye imaging optical apparatus recited in claim 1 wherein the optical window is in direct contact with the cornea of the eye or separated from the cornea with a thin layer of optically clear gel when the imaging apparatus is used to photograph the posterior of an eye.

7. The eye imaging optical apparatus recited in claim 1 wherein the eye structure or fundus is illuminated by the light emitted from a light source which then passes through a light conditioning device located behind the optical window, and outside and around the conical shaped lens.

8. The eye imaging optical apparatus recited in claim 1 wherein said eye imaging optical apparatus generates 3D stereoscopic images when two miniature cameras are used, and located effectively at the back focal plane of the miniature optical lens, and with their optical axes in parallel and separated by a small distance.

9. The eye imaging optical apparatus recited in claim 1 wherein said eye imaging optical apparatus generates 3D stereoscopic images when two miniature optical lenses are used together with two cameras located at the back focal plane of the miniature optical lenses, and with the optical axes of lens/camera module in parallel and separated by a small distance.

10. An eye imaging apparatus comprising:
    a housing;
    a light source disposed inside the housing and configured to illuminate an eye;
    an optical imaging system comprising:

an optical window with a radius of curvature closely matching a curvature of a cornea of the eye at a front end of the housing,
an imaging lens optically aligned with the optical window, the imaging lens positioned immediately behind and separated from the optical window by a gap filled with air,
at least first and second relay lenses, and
at least one miniature lens configured to form an image of the eye based on light received from the at least first and second relay lenses; and
a miniature image sensor configured to receive the image of the eye formed by the at least one miniature lens;
wherein a real image of an optical aperture in the at least one miniature lens is formed near an anterior surface of a crystalline lens of the eye when the eye imaging apparatus is being used to photograph a posterior segment of the eye.

\* \* \* \* \*